United States Patent [19]

Wikswo, Jr. et al.

[11] Patent Number: 5,109,196
[45] Date of Patent: Apr. 28, 1992

[54] METHOD AND APPARATUS FOR MAGNETIC IDENTIFICATION AND LOCALIZATION OF FLAWS IN CONDUCTORS BY CANCELING THE FIELD ABOUT THE CONDUCTOR WITH THE FIELD ABOUT A FLAWLESS CONDUCTOR

[75] Inventors: John P. Wikswo, Jr., Brentwood; Nestor G. Sepulveda; W. Patrick Henry, both of Nashville, all of Tenn.; Duane Crum, San Diego, Calif.

[73] Assignee: Vanderbilt University, Nashville, Tenn.

[21] Appl. No.: 664,640

[22] Filed: Mar. 5, 1991

[51] Int. Cl.⁵ .............................................. G01R 33/02
[52] U.S. Cl. ................................... 324/263; 324/232; 324/239
[58] Field of Search .............. 324/217, 218, 227, 225, 324/228, 232, 234–243, 262, 263; 361/267

[56] References Cited

U.S. PATENT DOCUMENTS

| | | | |
|---|---|---|---|
| 3,387,064 | 6/1968 | Joy et al. | 324/263 |
| 4,649,342 | 3/1987 | Nakamura | 324/252 X |
| 4,982,158 | 1/1991 | Nakata et al. | 324/263 |

FOREIGN PATENT DOCUMENTS 746278 7/1980 U.S.S.R. .

OTHER PUBLICATIONS

Harold Weinstock et al., Defect Detection with a Squid Magnetometer, Quantitative Nondestructive Evaluation, vol. 6, 1985 (publ. 1986) pp. 699–704.
Harold Weinstock et al., Nondestructive Evaluation of Metallic Structures Using a Squid Gradiometer, 3rd International Conference on Superconducting Quantum Devices, Jun. 25–28, 1985, Berlin (West).
M. Hashimoto et al., Nondestructive Testing Using Magnetic Field Visualization Technique, Review of Progress in Quantitative Nondestructive Evaluation, vol. 9, Edited by D. O. Thompson & D. E. Chimenti, Plenum Press, New York, 1990, pp. 585–592.

*Primary Examiner*—Kenneth A. Wieder
*Assistant Examiner*—Warren Edmonds
*Attorney, Agent, or Firm*—Richard V. Westerhoff

[57] ABSTRACT

Flaws in an electrically conductive sample object are detected by cancelling the magnetic field generated by a detection current passed through the sample object by passing the current back through an unflawed field cancelling object placed next to the sample object, and measuring the uncancelled field produced by any flaw, preferably with a superconducting quantum interference device (SQUID) magnetometer. Elongated objects such as tubes and rods are fed through a sleeve which forms the field cancelling object, with the current applied to the elongated member and passed to the field cancelling sleeve through sliding contacts.

20 Claims, 13 Drawing Sheets

METHOD AND APPARATUS FOR MAGNETIC IDENTIFICATION AND LOCALIZATION OF FLAWS IN CONDUCTORS BY CANCELING THE FIELD ABOUT THE CONDUCTOR WITH THE FIELD ABOUT A FLAWLESS CONDUCTOR

This invention was made under a contract awarded by the United States Department of the Air Force under Contract No. AFOSR-87-0337. The government has certain rights in this invention.

BACKGROUND OF THE INVENTION

1. Field of the Invention

This invention relates to non-destructive evaluation of electrically conductive objects by detecting the effects of flaws on the magnetic field generated by a current passed through the object. More particularly, the invention is directed to such a method and apparatus which includes cancellation of the magnetic fields produced by the edges of objects and the fields surrounding cylindrical objects to improve the relative signal strength of magnetic field disturbances attributable to flaws.

2. Background Information

One technique for non-destructive evaluation of electrically conductive objects is to pass an electric current through the object and observe disturbances in the magnetic field produced by the current resulting from flaws. Typically the component of the field perpendicular to the surface of the object is measured by a magnetometer. Superconducting quantum interference device (SQUID) magnetometers are very sensitive instruments which have been applied to detecting the very small disturbances in the magnetic field produced by flaws. However, features of the conducting object can generate much larger normal field components than the flaws. For instance, the edges of a conductive plate generate a large magnetic field component perpendicular to the surface of the plate. Also, the fields generated around rods and tubes and other such objects have a large normal component. These normal field components produced by features of an unflawed object mask the field generated by a flaw and thus reduce the sensitivity of such detection techniques.

The magnetic field surrounding the electric leads which apply the current to the conducting object is even greater than the field produced by the edges or the field surrounding a cylindrical object, because of the higher current density in the leads. As a result, it is even more difficult to locate flaws in the vicinity of the leads supplying current for the testing for flaws.

Thus, despite the high sensitivity of SQUID magnetometers, there have been limitations on the minimum size of flaws in the conducting object that can be detected by monitoring the magnetic field generated by a current applied to the object.

There is a need therefore for an improved method and apparatus for the non-destructive testing of conducting objects.

There is a more particular need for such method and apparatus which substantially reduces the effects of edges and of closed surfaces of an object on the magnetic field produced by a current passed through the object.

There is a further need for such a method and apparatus which can be used to test for flaws in elongated conducting objects as they are fed through a test station.

SUMMARY OF THE INVENTION

These and other needs are satisfied by the invention which is directed to detecting flaws in an electrically conductive sample object by placing an unflawed electrically conductive field cancelling object in spaced relation adjacent the sample object. A current is passed through the sample object in one direction and back through the field cancelling object in the opposite direction. The field cancelling object has a configuration which generates a magnetic field in response to the current which substantially cancels the magnetic field generated by the current passing through the sample object absent any flaws in the sample object. This reduces the normal component of the magnetic field produced by edges of planar objects and by curved closed surfaces on other objects so that a sensitive magnetometer can better discriminate the disturbance to the magnetic field produced by any flaws in the sample object. The strong fields generated by wires supplying the current to the sample object and the cancelling object are cancelled by using shielded leads, and preferably coaxial cables with one lead of the coaxial cable connected to the sample object and the other connected to a corresponding location on the field cancelling object.

For testing conducting plates, the field cancelling object is a similar plate having the same inhomogeneities as the sample plate. For testing tubes or rods, the field cancelling object can be a sleeve, or in the case of a tubular sample object, a rod or tube which may be inserted inside of the tubular sample. For large sample objects, it is not necessary that the field cancelling object be coextensive with the sample object. In fact, for planar objects, the field cancelling object can be a smaller plate which may be included in a unit with an array of magnetometers which can be scanned over the large planar sample. Long tube or rod samples can be fed through a shorter field cancelling sleeve with sliding brush contacts used to apply the current to the tubular or rod sample and to pass the current back from the tubular sample to the field cancelling sleeve. In a particularly advantageous arrangement, an annular SQUID magnetometer array surrounds the field cancelling sleeve with the superconducting shielding for the SQUIDs also shielding the tubular sample and the field cancelling sleeve from external magnetic fields.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
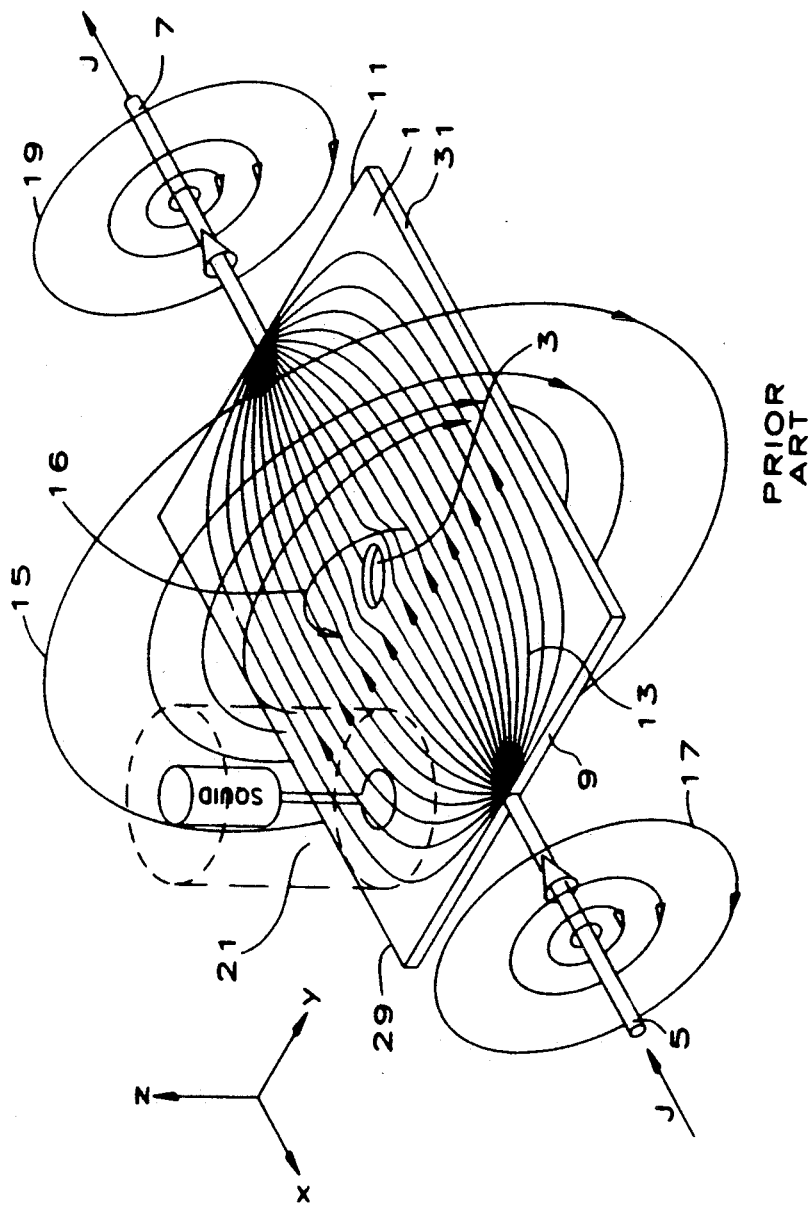
FIG. 1 is a schematic isometric view of a conducting plate with a hole in it to which a current is applied through a pair of wires and showing the current and magnetic field distributions without the benefit of the invention.

FIG. 1 illustrates a thin conducting plate 1 having a flaw in the form of a small circular hole 3 at the center. Wires 5 and 7 connected to opposite edges 9 and 11 of the plate 1 apply a current J from a remote current source (not shown) which flows through the plate 1 with the current distribution shown by the pattern 13. This current flowing through the plate generates a magnetic field 15. The hole 3 creates a disturbance 16 in the magnetic field 15. Magnetic fields 17 and 19 are also created by the current flowing through the wires 5 and 7, respectively. The Z component of the magnetic fields, that is a component normal to the plane of the plate 1, is measured by a magnetometer 21.

Figure 2:
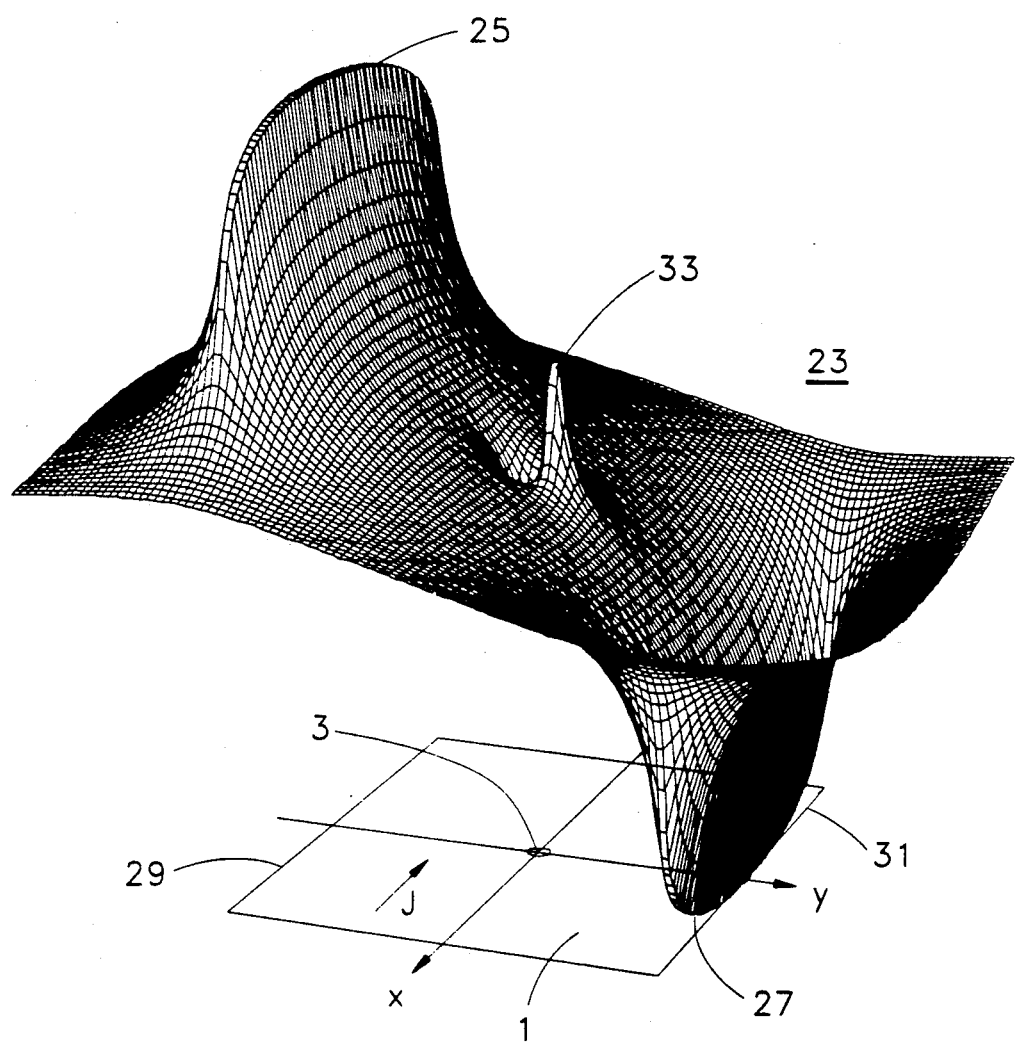
FIG. 2 is an isometric view of the Z component of the magnetic field for the plate of FIG. 1 without the contributions to the field produced by the wires.

FIG. 2 illustrates a plot of the Z component of the magnetic field produced by the current J flowing through the plate 1. As can be seen by FIG. 2, large Z components 25 and 27 are generated along the side edges 29 and 31 of the plate 1. The hole 3 generates a biphasic spike 33, which as can be seen, is much smaller in magnitude than the edge components 25 and 27. The Z component created by the wires 5 and 7 is not shown in FIG. 2.

Figure 3:
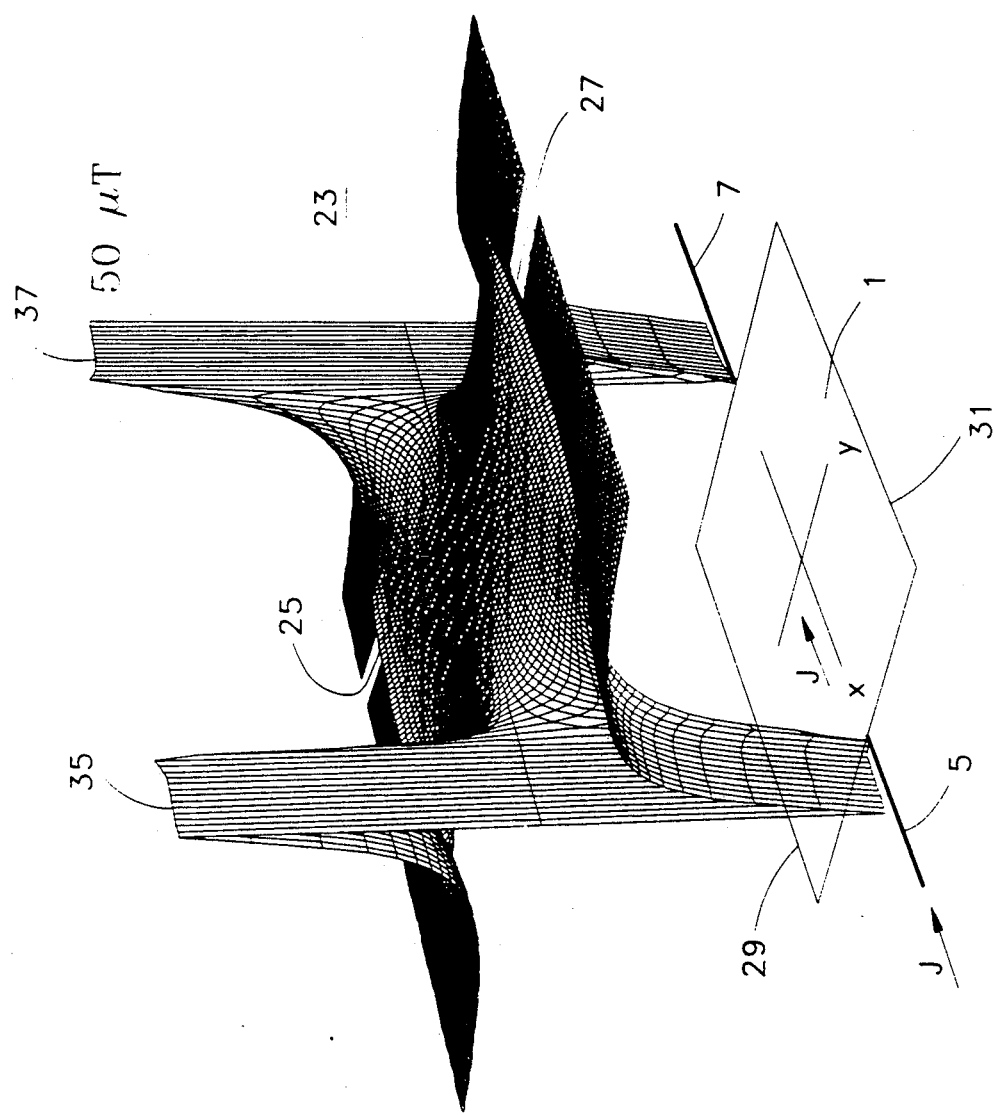
FIG. 3 is an isometric view of the Z component of the magnetic field of FIG. 2 to a much larger scale including the contributions to the field produced by the wires.

FIG. 3 illustrates the Z component 23 of the magnetic field including the components 35 and 37 produced by the wires 5 and 7. FIG. 3 is in much larger scale than FIG. 2, as can be seen by the relative heights of the components 25 and 27 generated by the side edges. The Z component 33 from the hole 3 is so small that it is not visible in FIG. 3. Thus, it can be seen that the Z component of the magnetic field due to the hole is considerably smaller than that due to the side edges and very much smaller than that due to the wires. Hence, identification of the flaw induced effect on the magnetic field is difficult with the prior art techniques.

Figure 4:
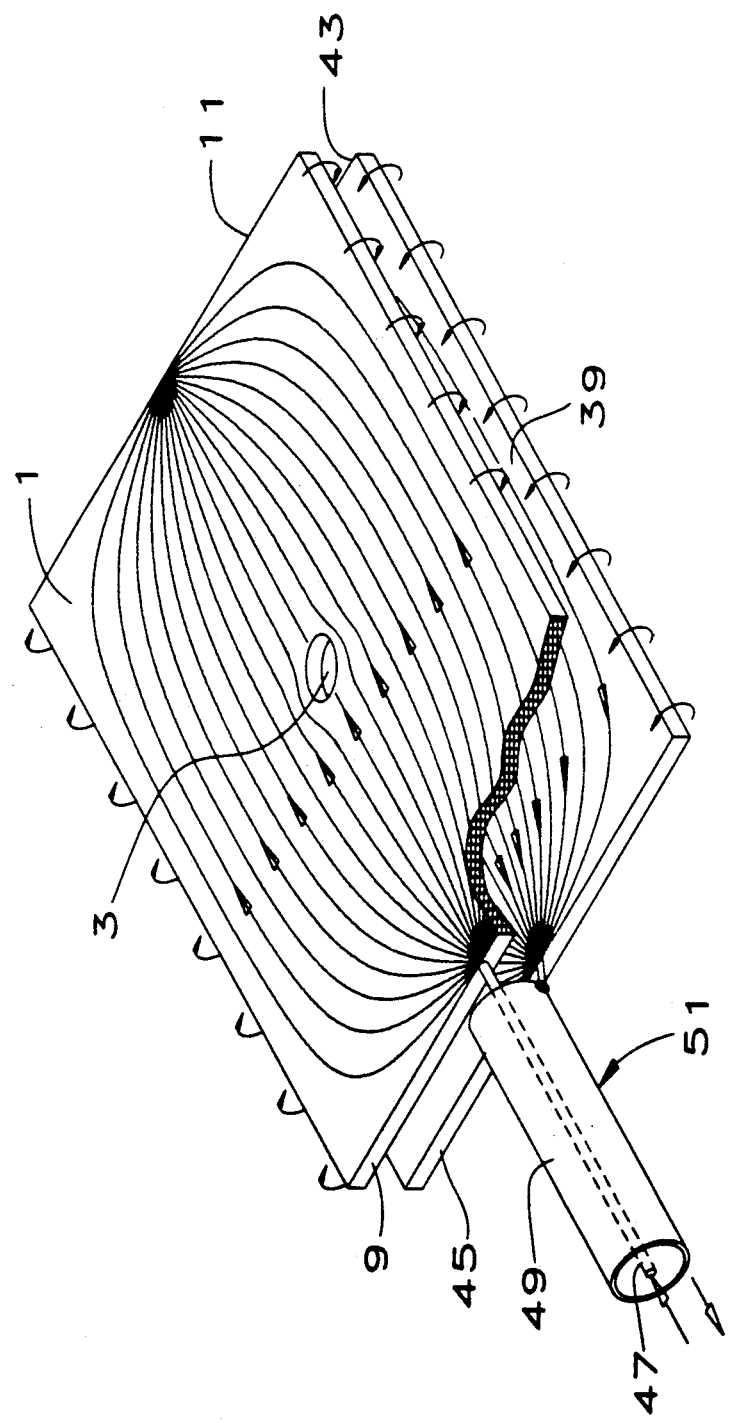
FIG. 4 is a schematic isometric view of an assembly of a conducting plate with a cancelling plate in accordance with one embodiment of the invention.
Figure 5:
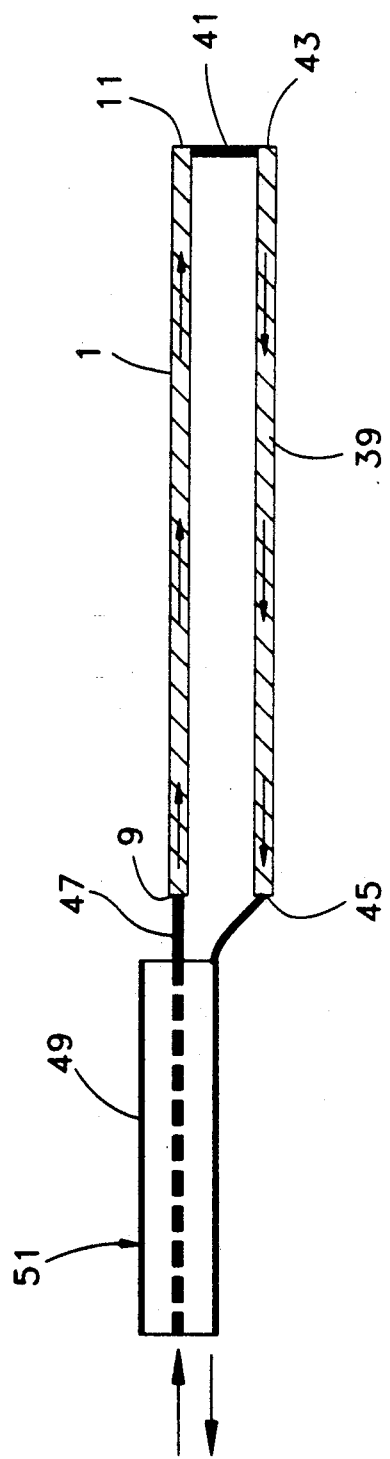
FIG. 5 is a schematic sectional view through the assembly of FIG. 4.

In accordance with the invention, the wire and edge fields are cancelled prior to mapping the magnetic field. As illustrated in FIGS. 4 and 5, a similar unflawed field cancelling object, in this case, a cancelling plate 39 is placed adjacent to the flawed plate 1, with an electrical connection 41 between the cancelling sheet 39 and the sample plate 1 at corresponding edges 11 and 43, and with the opposite edges 9 of the sample plate 1 and 45 of the cancelling plate 39 connected to the conductors 47 and 49, respectively, of a coaxial cable 51. Thus, an applied current will flow along one conductor of the cable 51, across either the sample plate 1 or the cancelling plate 39, across into the other plate through the electrical connection 41 and return through the other plate to the other conductor of the coaxial cable. As a result of this geometry, there is no magnetic field from the lead-in wires 47 and 49 because they are coaxial, and the magnetic field due to the edges of the sample plate 1 is cancelled by the opposing magnetic field of the edges of the adjacent field cancelling sheet 39.

Figure 6:
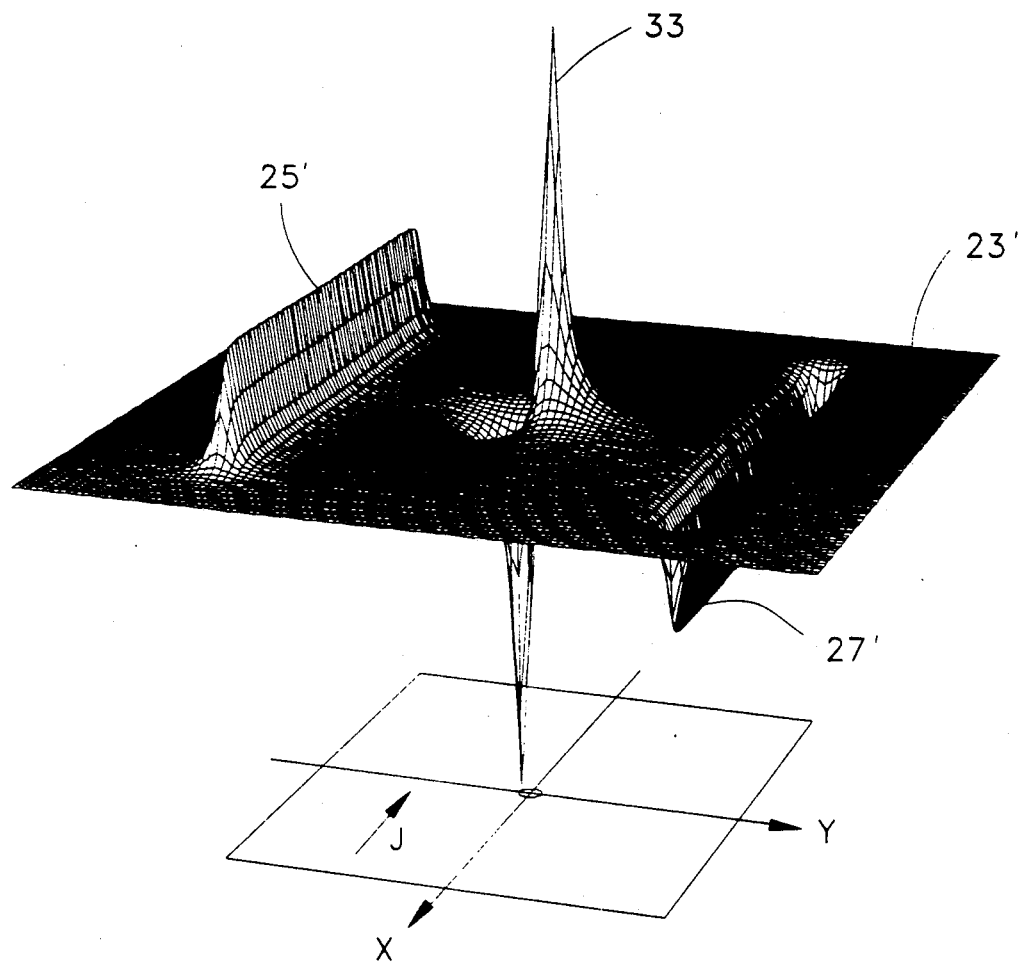
FIG. 6 is a schematic isometric view of the Z component of the magnetic field for the assembly shown in FIG. 4.

FIG. 6 illustrates a plot of the Z component of the magnetic field for the arrangement shown in FIGS. 4 and 5. As can be seen, the amplitude of the Z components 25' and 27' produced by the edges of the sample plate are greatly reduced relative to the amplitude of the biphasic Z component of the field 33 generated by the hole. The extent of cancellation is determined primarily by the separation between the sample plate 1 and the cancelling sheet 39 and by macroscopic inhomogeneities in their electrical conductivities. Ideally, there would be no vertical separation between the flawed plate and the cancelling plate. As shown in FIG. 6, there is only partial cancellation of edge effects if the plates are separated. The smaller the distance between the plates 1 and 39, the better is the removal of edge effects. If practical considerations provide a lower limit to the separation, the cancellation can be improved by adjusting the current in the returning plate to offset for the separation between the plates. However, an adjusted cancellation scheme requires the use of two different, highly regulated power supplies which is not practical in many situations, or the use of a current divider circuit. However, differences in the currents between the two plates will result in imperfect cancellation of the magnetic fields from the lead-in wires.

Figure 7:
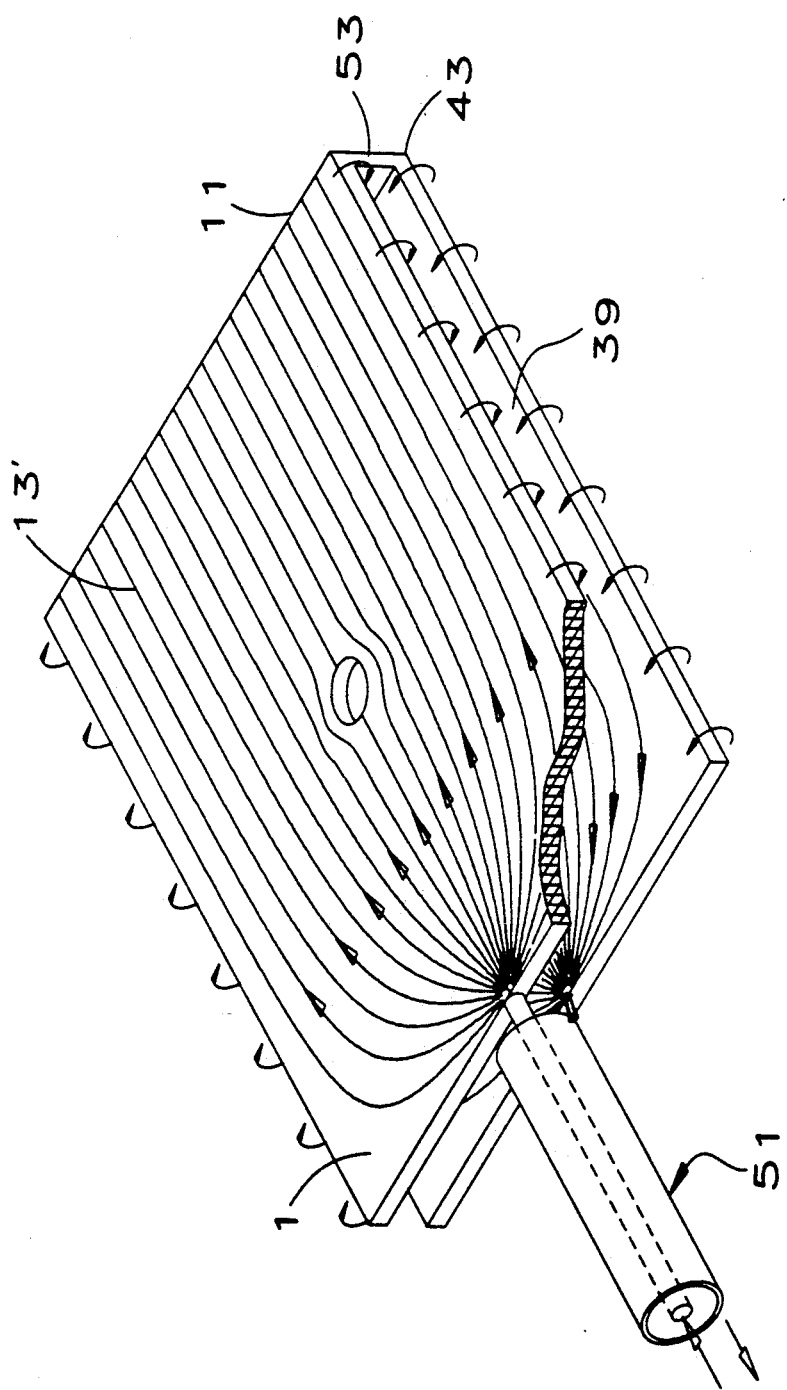
FIG. 7 is a schematic isometric view of an assembly of a conducting plate with a cancelling plate in accordance with another embodiment of the invention.

FIG. 7 illustrates another embodiment of the invention in which the sample plate 1 and field cancelling plate 39 are connected by an electrical connection 53 which extends along the entire length of the edges 11 and 43, respectively, and produces the current distribution 13'.

Figures 8A, 8B:
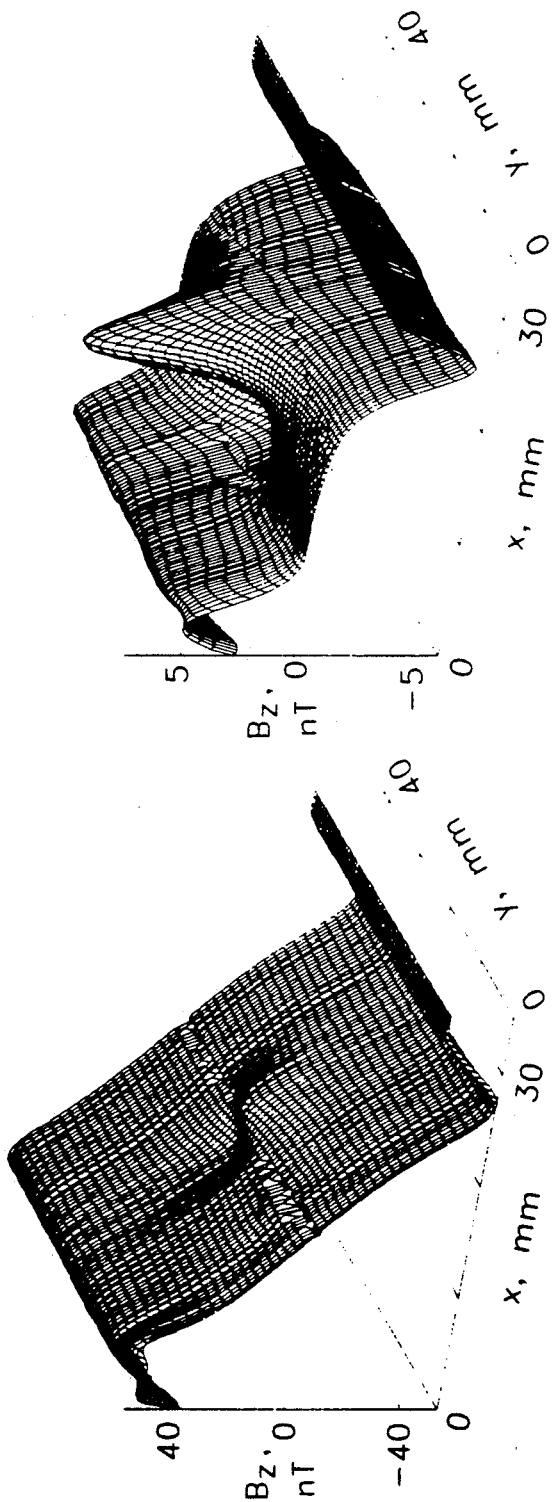
FIG. 8a is an isofield map of test data for a plate with a hole, but without the cancelling plate of the invention.
FIG. 8b is an isofield map of test data for the same plate with a hole and with a cancelling plate as shown in FIG. 7.

In order to verify the cancellation concept, a 25 mm × 150 mm × 32 μm thick copper sheet with a 3 mm diameter hole at its center was fabricated. A magnetic field map was obtained by passing a current of 7.5 mA through the flawed plate alone. The pickup coils of the high resolution SQUID magnetometers were scanned at 2.8 mm above the copper sheet. The data were acquired with a 1.6 Hz. sinusoidal excitation current using a digital lock-amplifier algorithm with an effective time constant of 630 mS. The edge field was almost an order of magnitude larger than that of the hole as shown by the isofield map of FIG. 8a. The addition of the cancelling plate in the configuration shown in FIG. 7 reduced the edge field by an order of magnitude, so that the hole field was larger than that from the edge as shown in FIG. 8b. Note the increased scale of FIG. 8b compared to FIG. 8a.

Figure 9:
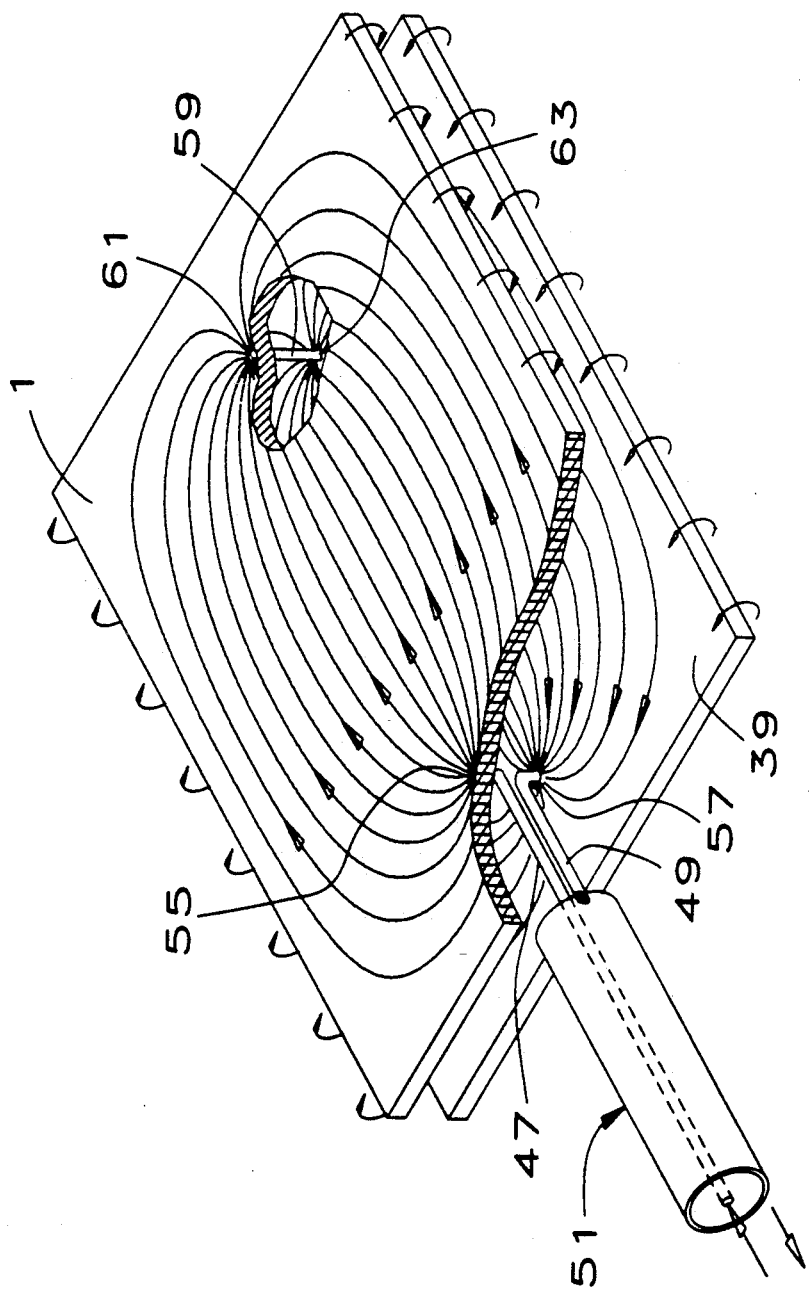
FIG. 9 is a schematic isometric view of an assembly of a conducting plate with a cancelling plate in accordance with yet another embodiment of the invention.

It is not necessary that the current be injected at the edges of the sample and field cancelling plate. Thus, as shown in FIG. 9, which illustrates another embodiment of the invention, the one conductor 47 of the coaxial cable 51 is connected to the sample plate at a point 55 spaced from the edges of the plate 1. The other conductor 49 of the coaxial cable 51 is connected to a corresponding point 57 spaced from the edges of the field cancelling plate 39. Similarly, the electrical connection 59 connects the plates 1 and 39 at corresponding remote points 61 and 63 spaced from the edges of the plates 1 and 39, respectively.

Figure 10:
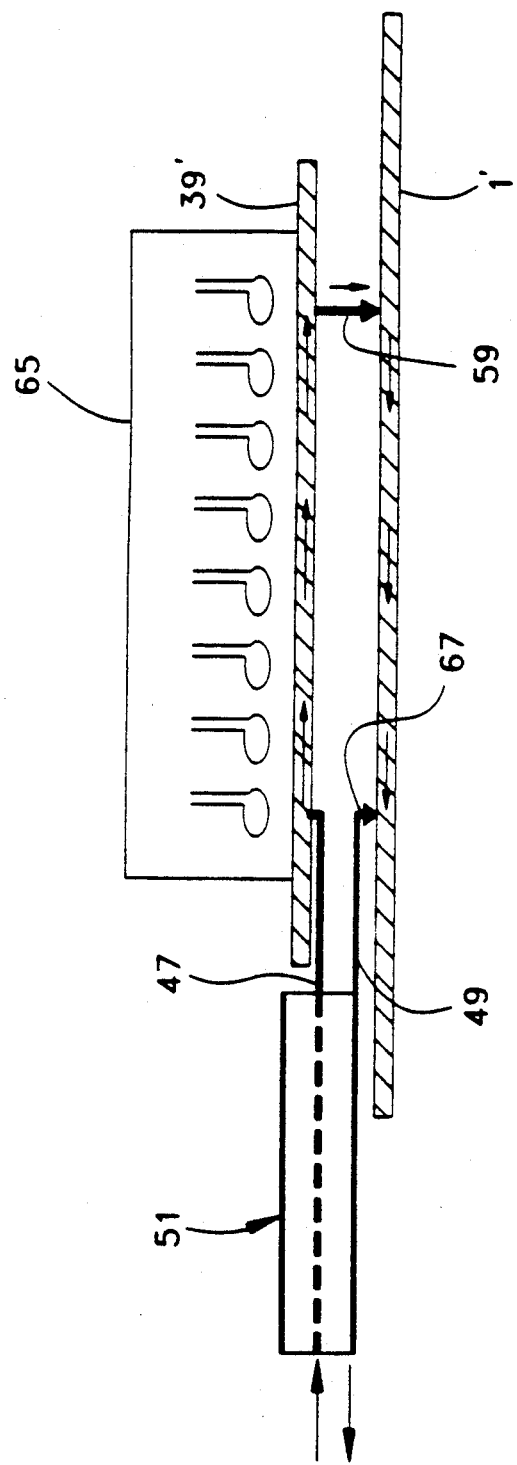
FIG. 10 is a schematic sectional view through an assembly similar to that of FIG. 9 including a magnetometer array.

As shown in FIG. 10, it is not necessary that the field cancelling plate be coextensive with a very large sample plate such as the plate 1'. In this embodiment of the invention, the current is only applied to a portion of the plate 1' to be tested. The field cancelling plate 39' is smaller than the plate 1', but larger in area than the portion of the sample plate 1' to which the test current is applied so that the corresponding points at which the current is injected into and extracted from the field cancelling plate 39' are spaced from the edges thereof. While this will produce some edge fields which are not fully cancelled, these edge fields will be smaller than those which would be produced by a pair of separate wires that would otherwise be required to pass current through the restricted region of the large plate. In this embodiment of the invention, a magnetometer array 65 is mounted on the field cancelling plate 39', and this unit can be scanned across the larger plate 1'. The electrical connections 67 and 59 make sliding contact with the larger plate 1'.

Figure 11:
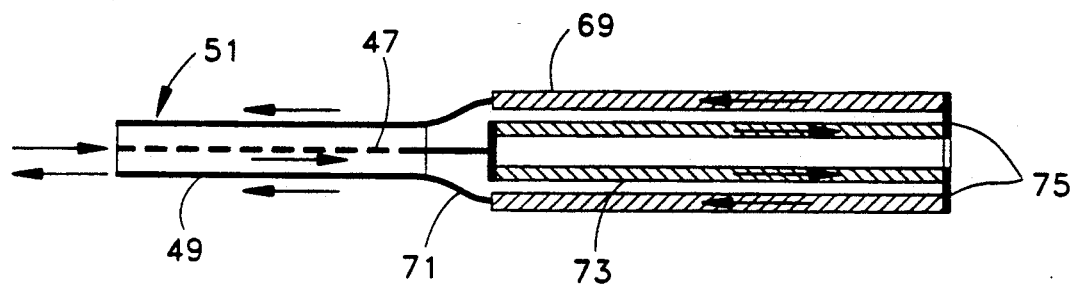
FIG. 11 is a schematic view of an application of the invention for testing tubular conducting samples.

FIG. 11 illustrates application of the invention to the testing of a tubular sample 69 which is connected to the outer conductor 49 of the coaxial cable 51 by a connecting ring 71. A cancelling tube 73 placed inside the tubular samples 69 is connected to the inner lead 47 of the coaxial cable 51 and through an end plug 75 to the remote end of the tubular sample 69. Alternatively, a rod can be substituted for the cancelling tube 73.

Figure 12:
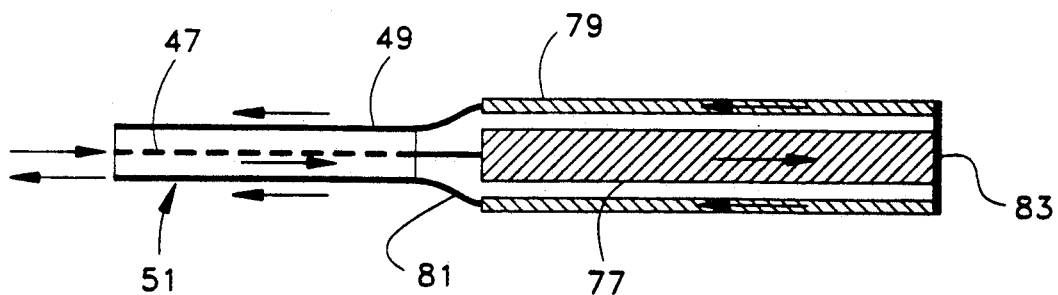
FIG. 12 is a schematic view of an application of the invention for testing a conducting rod sample.

FIG. 12 illustrates application of the invention to the testing of a rod sample 77 which is connected at one end to the inner conductor 47 of the coaxial cable 51. The sample rod 77 is encircled by a field cancelling tube 79 which is connected through a connecting ring 81 to the outer conductor 49 of the coaxial cable 51 and at the opposite end to the second end of the sample rod 77 through the plug 83.

Figure 13:
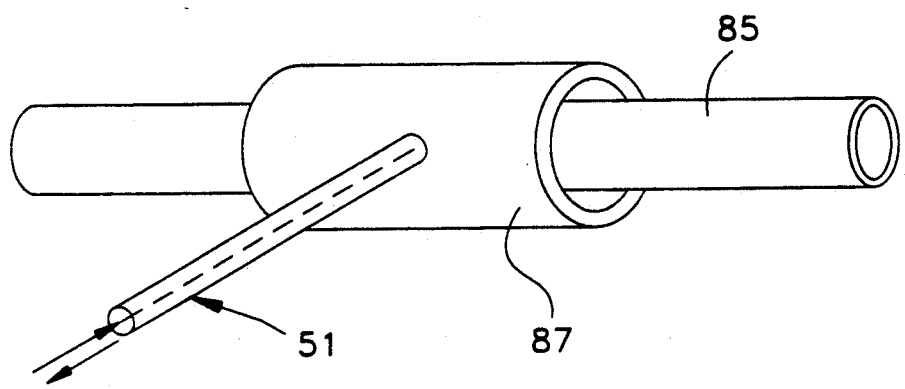
FIG. 13 is a schematic isometric representation of an application of the invention to testing long tubes.
Figure 14:
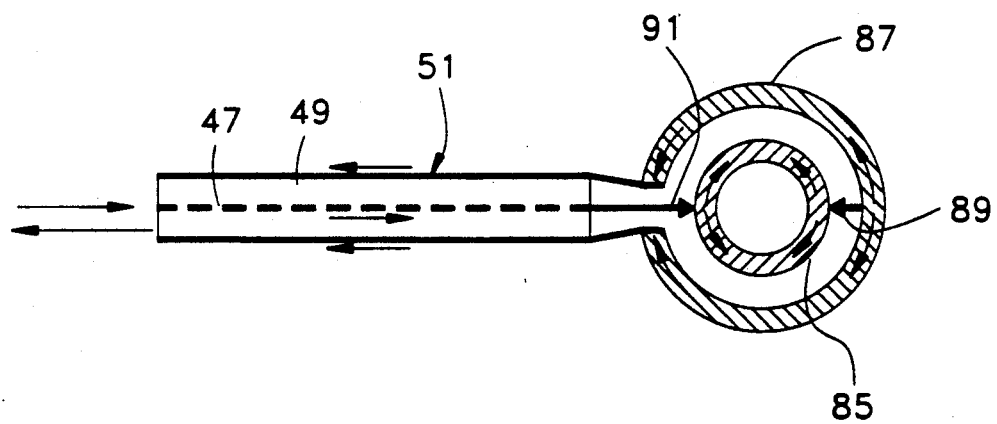
FIG. 14 is a schematic sectional view through the arrangement of FIG. 13.

FIGS. 13 and 14 illustrate an arrangement for testing for flaws in long tubes or rods. In this embodiment of the invention, the long sample tube or rod 85 is fed through a field cancelling tube 87 which is shorter than the length of the sample rod or tube. The field cancelling tube 87 is connected on one side to the outer conductor 49 of the coaxial cable 51. The opposite side of the cancelling tube 87 is connected to one side of the sample tube or rod 85 by a contact brush 89. Another contact brush 91 connects the opposite side of the sample rod or tube 85 to the inner conductor 47 of the coaxial cable 51. With this arrangement, the currents flow circumferentially through the sample tube or rod 85 and the cancelling tube 87, which is advantageous for detecting cracks which extend axially along the sample rod or tube 85.

Figure 15:
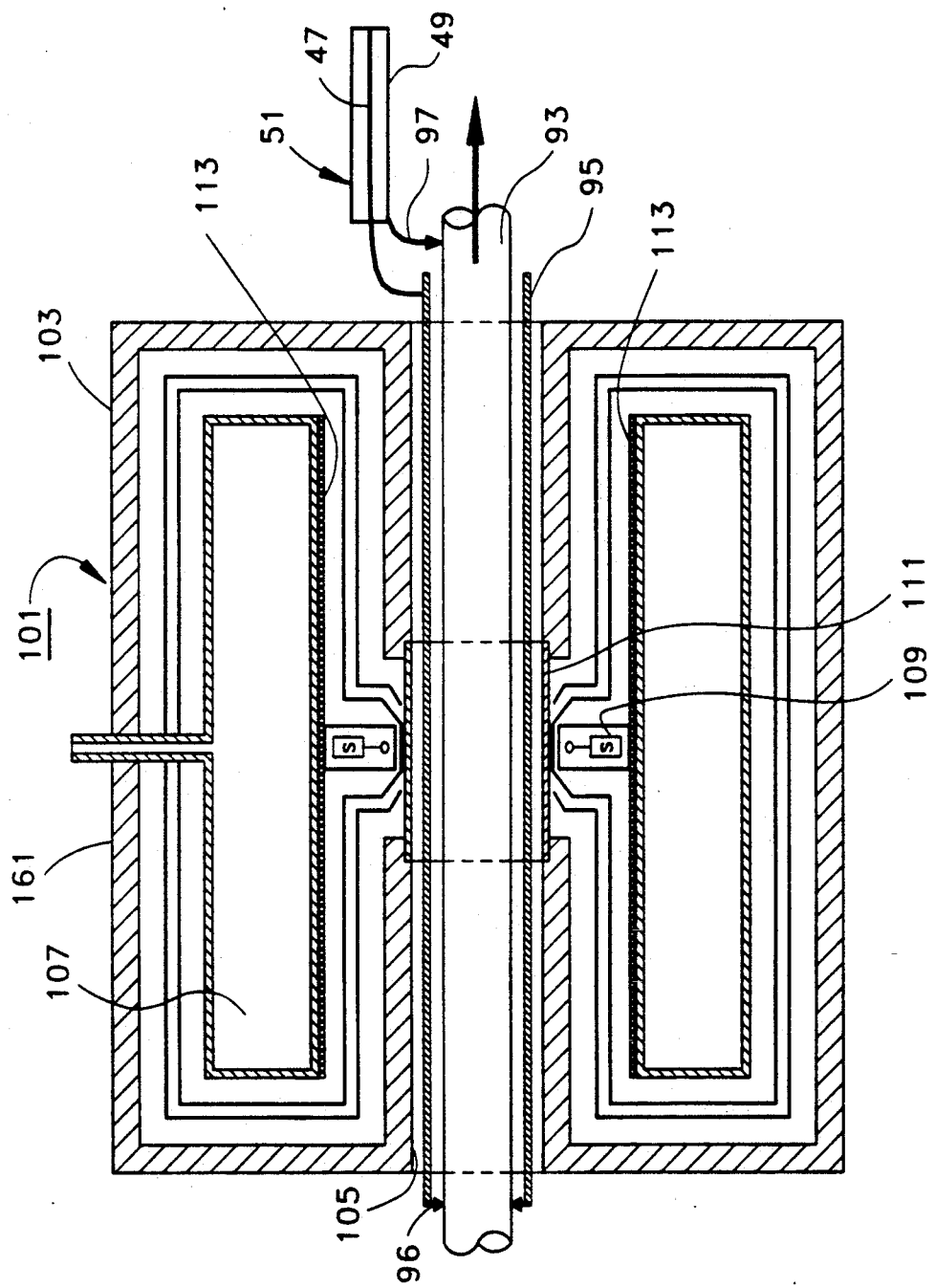
FIG. 15 is a schematic sectional view through a SQUID magnetometer adapted for testing long tubes and rods for flaws in accordance with the invention.

FIG. 15 discloses another embodiment of the invention for testing elongated rods or tubes for defects. In this arrangement, the sample rod or tube 93 is fed through a shorter field cancelling tube or sleeve 95. The sample tube or rod 93 is connected to the outer conductor 49 of the coaxial cable 51 through circumferentially distributed contact brushes 97 adjacent one end of the cancelling sleeve 95 which, in turn, is connected to inner conductor 47 of the coaxial cable. The opposite end of the cancelling tube or sleeve 95 is connected to the sample rod or tube 93 by circumferentially distributed contact brushes 96 so that the current flows axially through the cancelling sleeve 95 and the adjacent portion of the sample rod or tube 93.

The cancelling sleeve or tube 95 is surrounded by a SQUID magnetometer 101 which includes an annular cryostat 103 having a bore 105 through which the cancelling tube or sleeve 95 extends. A helium reservoir 107 stores liquid helium for cooling a ring of SQUIDs 109 extending around a window 111 in the bore 105 of the cryostat 103. A tubular superconducting shield 113 for the SQUIDs 109 also shields the cancelling tube 95, and the portion of the rod 93 being examined, from external magnetic fields.

The invention can be applied to testing for flaws in conducting objects of various shapes. The primary requirement is that the cancelling object have a configuration which substantially cancels the fields produced by the sample object without any flaws. Thus, for instance, an airplane wing could be tested using an anti-airplane wing as the cancelling object. As noted, the cancelling object can be smaller than a large sample object and can be scanned over the larger object, as long as the larger object is homogeneous over the portion scanned. The degree of inhomogeneity will, of course, affect the extent to which the non-flaw related fields can be cancelled, and therefore, the ability to detect flaws.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method of detecting flaws in an electrically conductive sample object comprising the steps of:

placing an unflawed electrically conductive field cancelling object in spaced relation adjacent said sample object;

passing a current through said sample object in one direction and back through the field cancelling object in an opposite direction, said field cancelling object having a configuration which generates a magnetic field in response to said current which substantially cancels a magnetic field generated by said current passing through said sample object absent any flaws in the sample object; and detecting any uncancelled magnetic field produced by flaws in said sample object.

2. The method of claim 1 wherein said detecting any uncancelled magnetic field comprises scanning said sample object with a magnetometer.

3. The method of claim 2 wherein said magnetometer is a superconducting quantum interference device magnetometer.

4. The method of claim 1 wherein said sample object and said field cancelling object are each planar objects each having a first edge and an opposite second edge, and wherein said step of passing current through said objects comprises applying said current to said sample object and field cancelling object adjacent said first edges thereof, and electrically connecting said sample